US007223268B2

(12) United States Patent
Biedermann

(10) Patent No.: US 7,223,268 B2
(45) Date of Patent: May 29, 2007

(54) LOCKING DEVICE FOR SECURING A ROD-SHAPED ELEMENT IN A HOLDING ELEMENT CONNECTED TO A SHANK

(75) Inventor: Lutz Biedermann, VS-Villingen (DE)

(73) Assignee: Biedermann Mötech GmbH (DE)

( * ) Notice: Subject to any disclaimer, the term of this patent is extended or adjusted under 35 U.S.C. 154(b) by 467 days.

(21) Appl. No.: 10/306,060

(22) Filed: Nov. 27, 2002

(65) Prior Publication Data

US 2003/0100904 A1    May 29, 2003

(30) Foreign Application Priority Data

Nov. 27, 2001 (DE) ................................. 101 57 814

(51) Int. Cl.
*A61B 17/58* (2006.01)
(52) U.S. Cl. .......................................... 606/61; 606/73
(58) Field of Classification Search .................. 606/61, 606/72, 73
See application file for complete search history.

(56) References Cited

U.S. PATENT DOCUMENTS 6,063,090 A * 5/2000 Schlapfer ..................... 606/61
6,074,391 A   6/2000 Metz-Stavenhagen et al.
6,077,262 A * 6/2000 Schlapfer et al. ............. 606/61
6,224,598 B1   5/2001 Jackson
6,835,196 B2 * 12/2004 Biedermann et al. ......... 606/61
2004/0249380 A1 * 12/2004 Glascott ....................... 606/73
2005/0171537 A1 * 8/2005 Mazel et al. .................. 606/61

FOREIGN PATENT DOCUMENTS

| EP | 280 748 | 9/1988 |
|---|---|---|
| GB | 258106 | 9/1926 |
| WO | WO 96/01132 | 1/1995 |
| WO | 298 10 798 U1 | 12/1999 |

* cited by examiner

*Primary Examiner*—Eduardo C. Robert
*Assistant Examiner*—James L. Swiger
(74) *Attorney, Agent, or Firm*—Christie, Parker & Hale, LLP.

(57) ABSTRACT

An element with a shank (1) and a holding element (2; 21; 21') connected to it for connecting to a rod (100) is provided, wherein the holding element (2; 21; 21') has a recess having a U-shaped cross-section for receiving the rod with two legs (4, 5; 26, 27) open at one end (6, 28) and an inner thread (7; 29) on the open legs and with a locking element (8; 80) with an outer thread (9) in at least one section of its outer wall, wherein the outer thread (9) cooperates with the inner thread (7; 29) of the legs and wherein the locking element has a central bore, characterised in that the locking element (8, 80) has a slit (14) extending substantially in the axial direction through its outer wall.

18 Claims, 5 Drawing Sheets

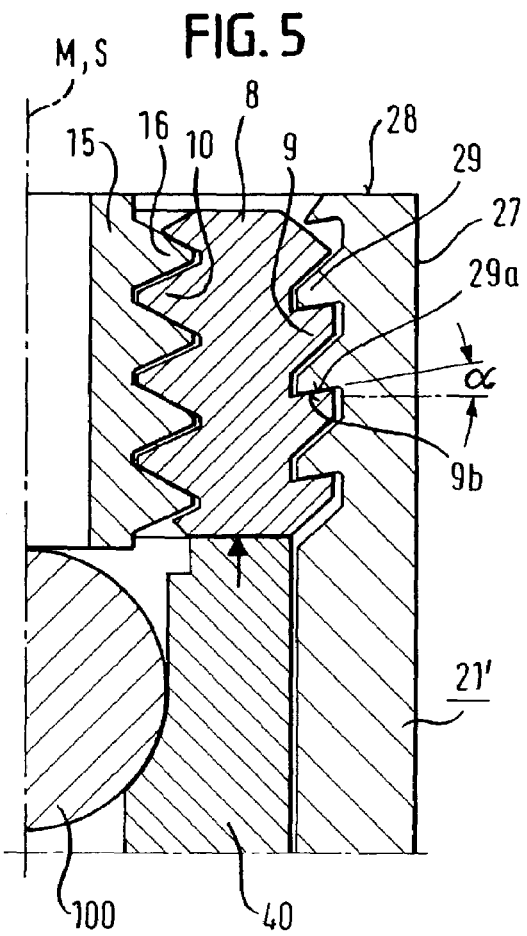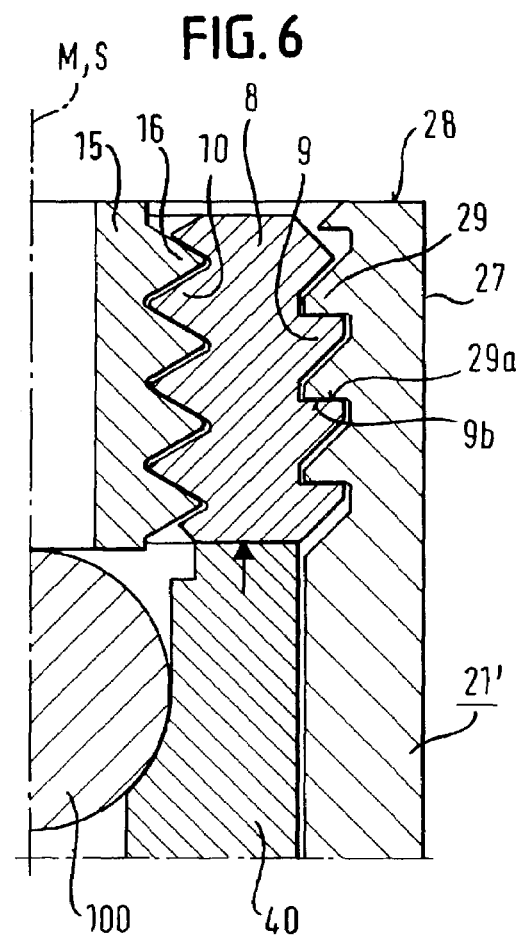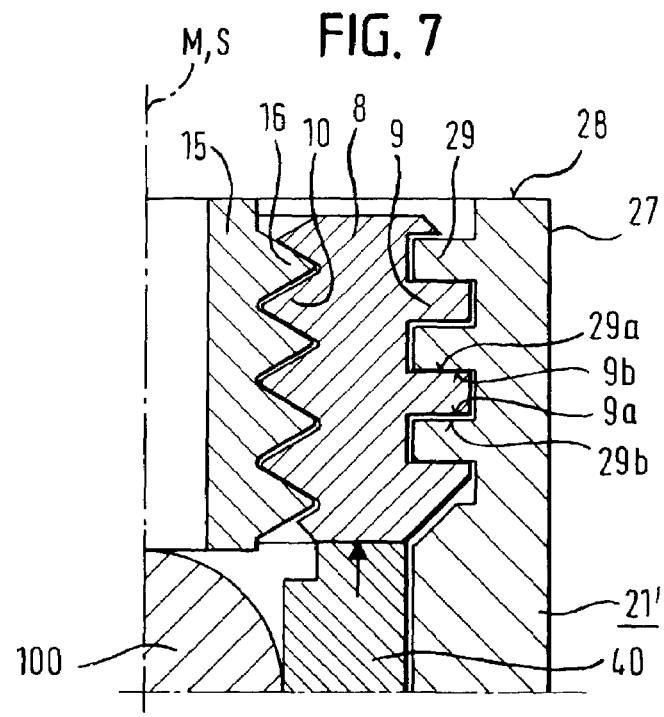

LOCKING DEVICE FOR SECURING A ROD-SHAPED ELEMENT IN A HOLDING ELEMENT CONNECTED TO A SHANK

The invention relates to a locking device for use in spinal column or accident surgery for securing a rod-shaped element in a holding element connected to a shank. The invention further relates to an element with a shank and a holding element connected to it for connecting to a rod with a locking device of this kind.

From WO 95/01132 and U.S. Pat. No. 6,224,598 B1 a spinal column implant with a receiving part with a U-shaped recess for receiving a rod is known, respectively, wherein the open legs formed by the U-shaped recess have an inner thread. To fix the rod a locking element, which can be screwed in between the legs, with an outer thread, a central bore with inner thread and an inner screw which can be screwed into the locking element is provided. In the device known from WO 95/01132 a security sleeve encircling the legs from outside is used to avoid splaying of the legs.

It is the object of the invention to create a locking device of the kind initially described which guarantees improved security against loosening or detaching of the locking elements and at the same time is compactly built and easy to produce.

This object is achieved by the locking device characterised in claim 1 or by the element characterised in claim 5. Further developments of the invention are given in the subordinate claims.

The invention is suitable for both monoaxial and polyaxial bone screws, as it allows fixing of the rod or the rod and the head of the bone screw in the final state to cooperate in such a way that there is secure blocking against loosening or detaching of the locking mechanism.

Further features and advantages of the invention emerge from the description of embodiment examples using the figures.

FIG. 2a shows a schematic illustration of the forces acting on the locking element of FIG. 1 before the inner screw is screwed in.

FIG. 2b shows a schematic illustration of the forces acting on the locking element of FIG. 1 after the inner screw has been screwed in.

FIG. 5 shows a sectional view of a detail of a fourth embodiment.

FIG. 6 shows a sectional view of a detail of a fifth embodiment.

FIG. 7 shows a sectional view of a detail of a sixth embodiment.

Figure 1:
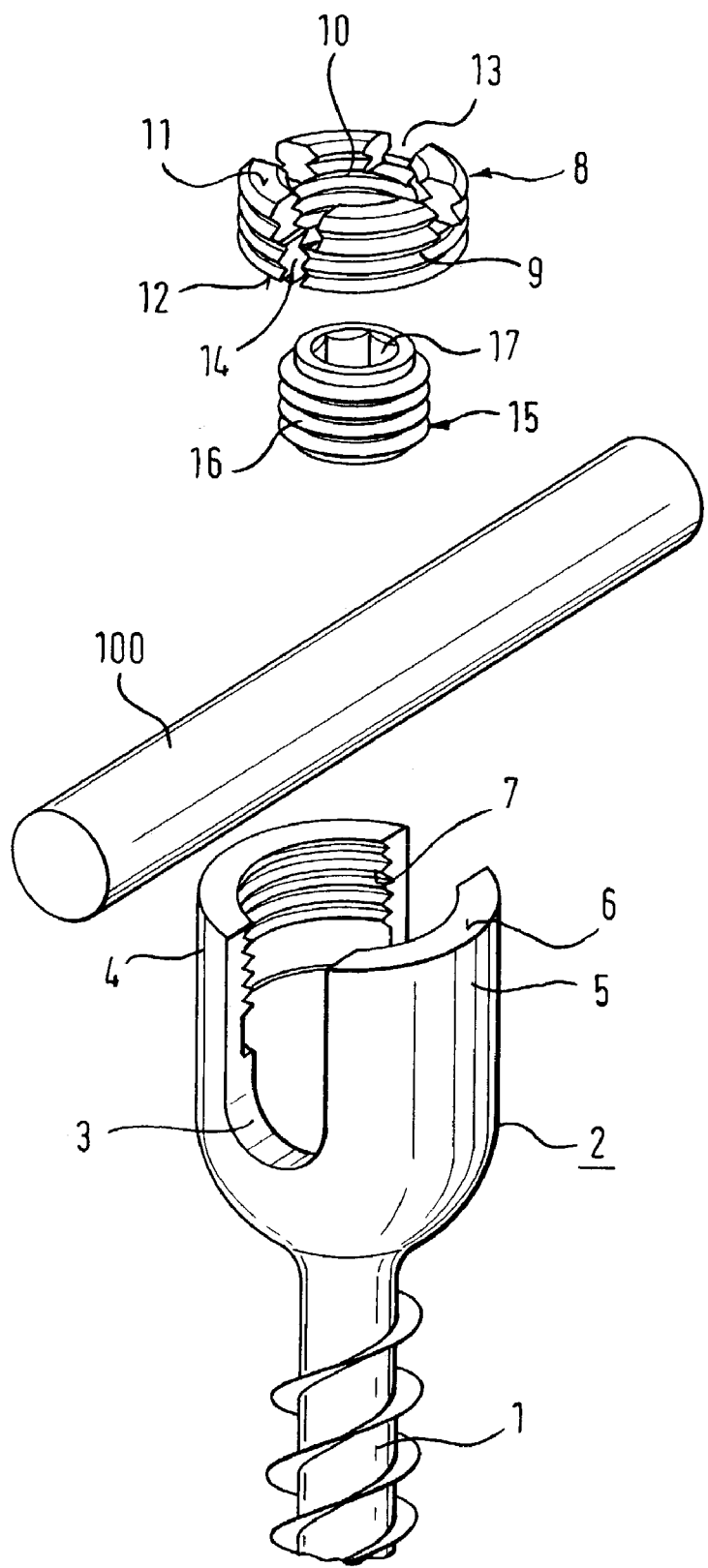
FIG. 1 shows a first embodiment in perspective exploded illustration.

The element according to the invention in the embodiment illustrated in FIG. 1 of the figures is constructed as a monoaxial bone screw. It has a shank 1 with a bone screw section and a receiving part 2, rigidly connected to it, for receiving a rod 100 connecting the bone screw to further bone screws. For this purpose the receiving part is provided with a recess 3 with a U-shaped cross-section, which is dimensioned just large enough for the rod 100 to be placed in and fit into the bottom of the recess. By the U-shaped recess 3 two open legs 4, 5 are formed with in each case one open end 6, which forms the upper edge of the receiving part 2. The legs 4, 5 have an inner thread 7 adjacent to the open end 6.

To lock the rod 100 in the recess 3 a sleeve-type or nut-type locking element 8, which can be screwed in between the legs 4, 5, is provided, with an outer thread 9 cooperating with the inner thread 7 of the legs and an inner thread 10. The locking element 8 has a first front end 11 and opposite this a second end 12. Radially running notches 13 are provided on the first front end 11 for bringing into engagement with a screwing in tool. One of the notches extends through the entire locking element 8 in the axial direction and thus forms a slit 14 in such a way that the locking element has a certain elasticity in the manner of a straining ring. The length of the locking element 8 in the axial direction is dimensioned in such a way that the locking element can be fully screwed in between the legs 4, 5.

Further provided is an inner screw or clamping or set screw 15, which can be screwed into the locking element and the outer thread 16 of which cooperates with the inner thread 10 of the locking element 8. The inner screw 15 has on one of its ends a recess 17 for bringing into engagement with a screw tool.

In the embodiment shown in FIG. 1 the inner thread 7 of the legs, the outer thread 9 of the locking element and also the inner thread 10 of the locking element and the outer thread 16 of the inner screw 15 are formed as metric threads.

Figure 2A:
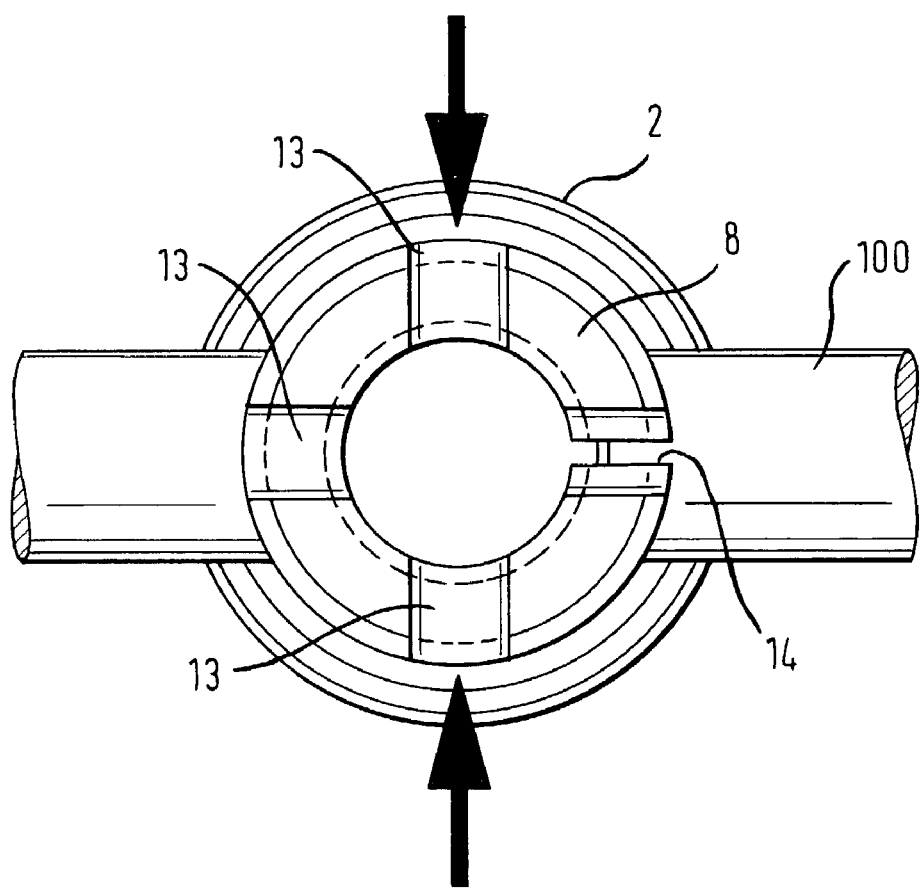
Figure 2B:
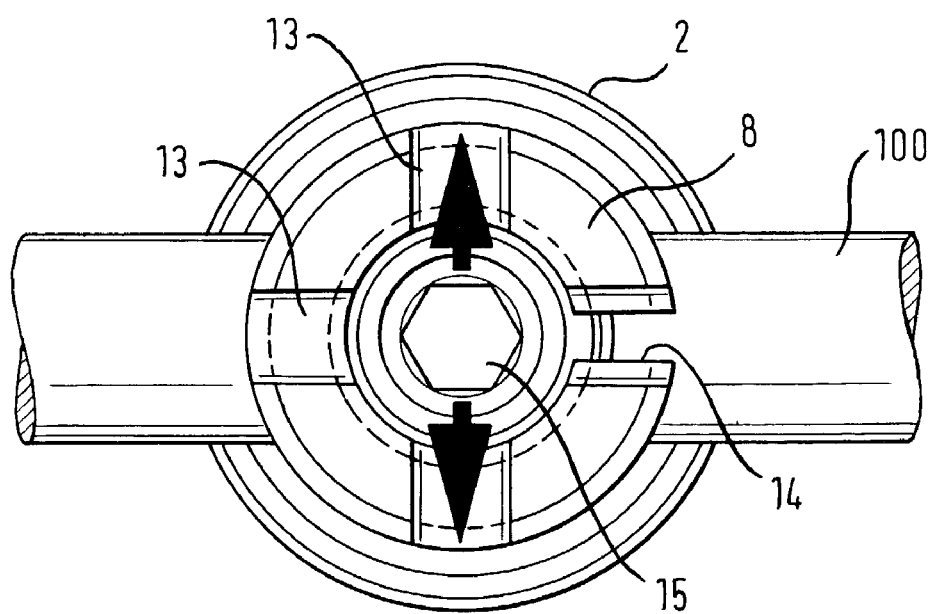

In operation the bone screw 100 is first screwed into the bone and then the rod 100 is placed in. The locking element 8 is then screwed in with the inner screw 15 already screwed in, but not yet touching the rod with its underside, whereby the rod is at first only prevented from tilting out, but is still displaceable. When the locking element 8 is screwed in no splaying of the legs 4, 5 arises, owing to the slit and therefore elastic construction, but, as shown in FIG. 2a, the legs put up a resistance to the slit locking element, which tries to press it together, as depicted by the inwardly directed arrows. The inner screw 15 is then screwed in until it presses with its underside on the rod and fixes it. Owing to the tightening of the inner screw 15, a radially outwardly directed force component acts on the locking element 8, as illustrated by the arrows in FIG. 2b, whereby the outer thread 9 of the locking element is pressed into the inner thread 7 of the legs and is there blocked. This guarantees locking secured against loosening.

Figure 3:
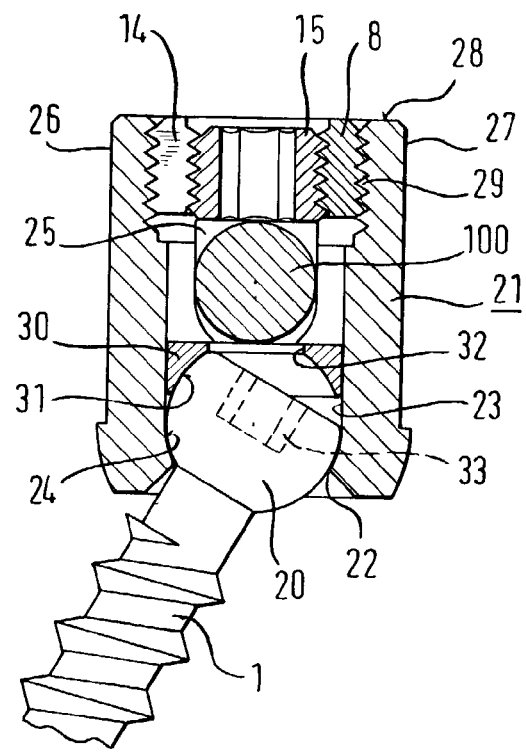
FIG. 3 shows a sectional view of a second embodiment.

In the embodiment shown in FIG. 3 the element according to the invention is constructed as a polyaxial screw which has a screw element with a thread shank 1 with a bone thread and a head 20 shaped like a segment of a sphere, which is connected to a receiving part 21. The receiving part 21 has on one of its ends a first bore 22, aligned symmetrically to the axis, the diameter of which is larger than that of the thread section of the shank 1 and smaller than that of the head 20. The receiving part 21 further has a coaxial second bore 23, which is open at the end opposite the first bore 22 and the diameter of which is large enough for the screw element to be inserted through the open end with its thread section through the first bore 22 and with the head 20 as far as the bottom of the second bore 23. Between the first and the second bore a small coaxial section 24 is provided, which is immediately adjacent to the first bore 22 and is constructed as spherical towards the open end, wherein the radius is substantially identical to the section of the head 20 shaped like a segment of a sphere. Receiving part 21, like receiving part 2 of the first embodiment, has a U-shaped recess 25, arranged symmetrically to the centre of the part, the bottom of which is directed towards the first bore 22 and by which two open legs 26, 27 are formed, the open end 28 of which forms the edge of the receiving part 21. The legs 26, 27 have an inner thread 29 in an area adjacent to the open end 28.

Further provided is a pressure element 30, which is constructed in such a way that on its side facing the head 20 it has a spherical indentation 31, the radius of which is substantially identical to the radius of the section of the head 20 shaped like a segment of a sphere. The outer diameter of the pressure element is chosen in such a way that the pressure element can perform a sliding movement in the receiving part 21, in other words is displaceable towards the head 20. The pressure element further has a coaxial bore 32 for access to a recess 33 in the screw head 20 for bringing into engagement with a screwing in tool.

Construction of the locking element 8 and the inner thread 15 is as in the first embodiment.

In operation the screw element is screwed into the bone after being placed into the receiving part 21. The pressure element 30 and the rod 100 are then inserted in turn. At this stage the screw head 20 is still swivellable. By screwing in the locking element 8 and the inner thread 15 in the same way as in the first embodiment the screw element and the receiving part 21 are fixed to one another and therefore the rod 100 is also fixed.

Figure 4:
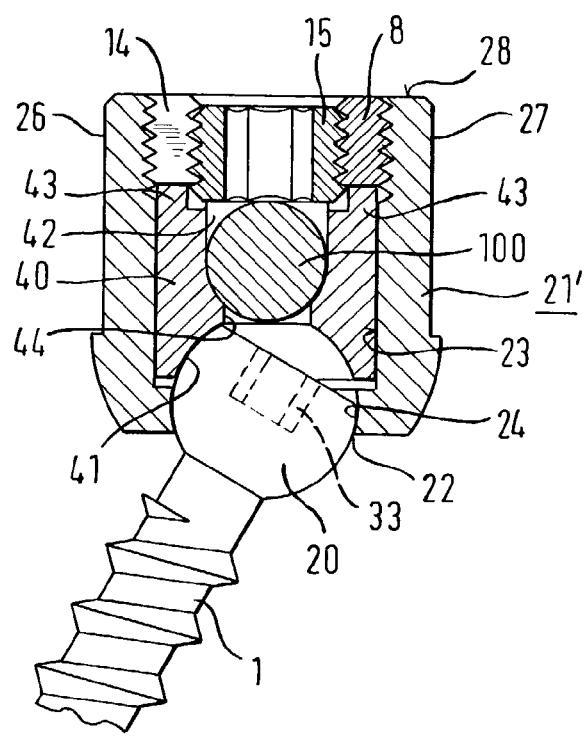
FIG. 4 shows a sectional view of a third embodiment.

The third embodiment illustrated in FIG. 4 also shows a polyiaxial bone screw. Parts corresponding to the second embodiment are provided with the same reference numerals. The third embodiment differs from the second embodiment substantially in the construction of the pressure element 40.

The pressure element 40 of this embodiment is substantially constructed as cylindrical with an outer diameter which is chosen in such a way that the pressure element 40 can slide in the second bore 23 of the receiving part 21'. On one of its ends a recess 41, shaped like a segment of a sphere and widening towards the end is provided, the sphere radius of which is chosen in such a way that, in a state inserted into the receiving part, it partially encircles the head 20 of the screw element. A substantial difference from the pressure element 30 of the second embodiment is that the pressure element 40 of the third embodiment is lengthened in the direction of the open end 28 of the legs. For this purpose it has on its end opposite the recess 42 shaped like a segment of a sphere a U-shaped recess 42, wherein the dimensions of the U-shaped recesses of the pressure element are such that the rod 100 can be placed in the channel formed thereby. The depth of the U-shaped recess 42, seen in the direction of the cylindrical axis of the receiving part 21' is larger than the diameter of the rod 100 to be received, so that the pressure element 40 projects upwards above the placed in rod 100 with lateral legs 43. The pressure element 40 further has a central bore 44 extending therethrough. The diameter of the central bore 44 is just large enough for a screw tool for bringing into engagement with the recess 33 provided in the head 20 to be guided through.

Construction of the locking element 8 and the inner thread 15 is as in the first and second embodiments.

In operation the third embodiment shown in FIG. 4 differs from the second embodiment shown in FIG. 3 in that via the locking element 8 the head 20 is first blocked in its position, in which the locking element 8 presses on the lengthened legs 43 of the pressure element 40 and therefore on the head 20. By tightening the inner screw 15 the rod 100 is then fixed independently of the head 20. The locking effect caused by the cooperation of locking element 8 and inner screw 15 is otherwise as in the first and second embodiments.

The embodiments shown in FIGS. 5 to 7 differ from the third embodiment shown in FIG. 4 in the type of inner thread 7 of the legs 26, 27 of the receiving part 21' and the corresponding outer thread 9 of the locking element 8. The inner thread 10 of the locking element 8 and the outer thread 16 of the inner screw are constructed in these embodiments in each case as metric threads.

In the embodiment shown in FIG. 5 the inner thread 29 of the legs 26, 27 is constructed in such a way that the flank 29a facing away from the open end encloses a negative angle a with a plane running perpendicular to the central axis M of the receiving part. Correspondingly, flank 9b of the outer thread 9 of the locking element 8 facing away from the open end in the screwed in state encloses a negative angle with a plane running horizontally to the screw axis S. The dimensions of the inner thread of the legs and the outer thread of the locking element are such that in the unloaded state there is a gap between the flanks 29a and 29b mentioned.

In operation the legs 26, 27 experience a force component directed radially inwards owing to the negative flank angle when the locking element 8 is tightened, wherein the flanks 29a and 10b come to be on top of one another, so the legs are slightly pulled together. This gives rise to reliable blocking of the head 20 via the pressure element 40. When the inner screw is screwed in, the locking element 8 splays out owing to the force component which is then acting radially outwards and therefore acts against the force pulling the legs together. The rod is fixed and simultaneously blocking of the locking element 8 and legs against one another takes place.

The embodiment shown in FIG. 6 differs from the embodiment shown in FIG. 5 in the construction of the threads 28, 9 as saw tooth threads with a load flank 29a or 19b running horizontally to the central axis M or screw axis S. This also demonstrates the function according to the invention of the locking element.

The embodiment shown in FIG. 7 differs from the embodiment shown in FIGS. 5 and 6 in that the inner thread 29 of the legs and the outer thread 9 of the locking element are constructed as a flat thread. This has two flanks 29a, 29b or 9a, 9b, running horizontally to the central axis M or screw axis S. The thread cross-section is constructed as substantially rectangular. This also demonstrates the function according to the invention of the locking element.

A flank play is also provided in the thread forms shown in FIGS. 6 and 7 in such a way that blocking of the locking element is possible after the inner screw has been screwed in.

Figure 8:
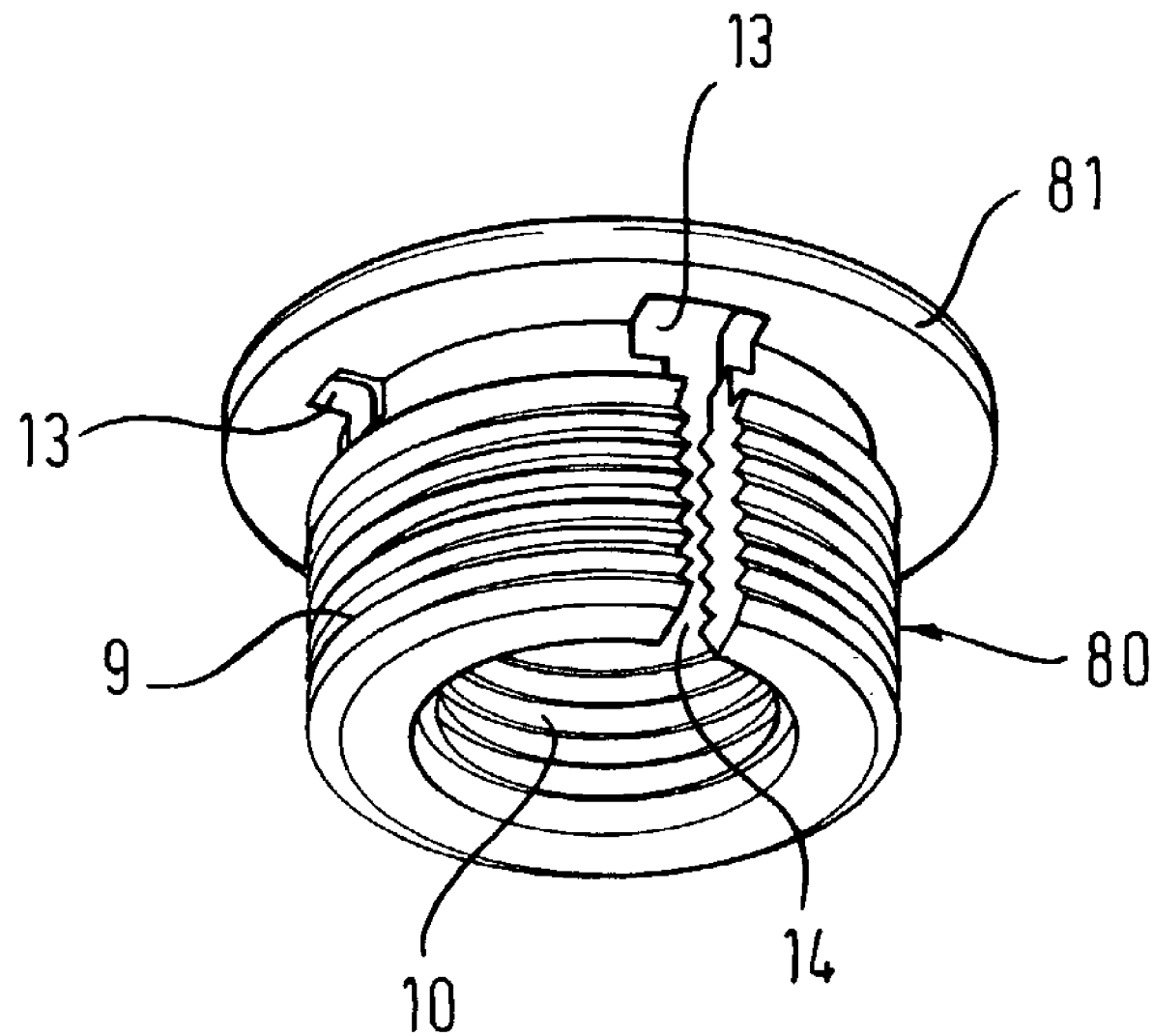
FIG. 8 shows a sectional view of a detail of a seventh embodiment.

In the embodiment shown in FIG. 8 the locking element 80 is provided with a ring-shaped projection 81 on its front end which has the notches 13. The slit 14 extends in this case, as in locking element 8, at least through the axial section in which the outer thread 9 is provided, but not through the projection 81. The slit 14 is further arranged in the circumferential direction in such a way that it extends into one of the notches 13.

In operation, when the locking element is screwed in, the projection 81 forms a stop which limits the force on the pressure element to a predetermined value.

Further embodiments of the invention emerge from the provision of the types of thread according to the embodiments according to FIGS. 5 to 6 and/or the locking element according to FIG. 8 in a monoaxial screw according to the first embodiment according to FIG. 1 or the polyaxial screw according to the second embodiment according to FIG. 3.

Instead of the above-described embodiments, in which the receiving part is connected to a bone screw, the receiving part can also be connected to a hook, as used in spinal column surgery for hooking in behind bone projections of the spinal column.

In a further modification of the polyaxial embodiments, instead of the thread shank 1 or the hook, a bar or a rod-shaped element is provided, which has on both ends a head shaped like a segment of a sphere, which is connected to a receiving part of the kind described. In this way an element of this kind can be used as a connecting element between two rods 100.

What is claimed is:

1. A holding device comprising:
   a shank portion;
   a holding portion connected to the shank portion for holding a rod; and
   a locking element to lock the rod in the holding portion;
   wherein the holding portion comprises a recess on one end having a U-shaped cross-section and two open legs for receiving the rod, and a first inner thread on the open legs;
   wherein the locking element comprises a front end that faces out of the recess when fastened to the holding portion and an opposite back end that faces into the recess when fastened to the holding portion, a wall surrounding a central bore, an outer thread in at least one section of the wall, the outer thread cooperating with the first inner thread on the open legs, and a slit extending substantially in an axial direction completely through the wall from the front end to the back end.

2. The holding device according to claim 1, wherein the locking element has a second inner thread, the holding device further comprising an inner screw having an exterior thread for cooperating with the inner thread of the locking element.

3. The holding device according to claim 2, wherein an angle position of the shank can be fixed by the locking element.

4. The holding device according to claim 2, wherein the rod can be fixed by the inner screw of the locking element.

5. The holding device according to claim 1, wherein the inner thread of the locking element and the exterior thread of the inner screw comprise metric threads.

6. The holding device according to claim 1, wherein the inner thread of the legs comprises a metric thread.

7. The holding device according to claim 1, wherein the inner thread of the legs comprises a load flank with a negative flank angle.

8. The holding device according to claim 1, wherein the inner thread of the legs comprises a saw tooth thread having a substantially horizontal load flank.

9. The holding device according to claim 1, wherein the inner thread of the legs comprises a flat thread having two horizontal flanks.

10. The holding device according to claim 1, wherein the locking element further comprises a stop.

11. The holding device according to claim 1, wherein the shank portion and the holding portion are monoaxially connected.

12. The holding device according to claim 1, wherein the shank portion and the holding portion are polyaxially connected.

13. The holding device according to claim 1, further comprising a pressure element in the holding portion, which cooperates with the locking element to fix an angle position of the shank.

14. A holding device comprising:
    a shank portion;
    a locking portion connected to the shank portion for holding a rod; and
    a locking element to lock the rod in the holding portion;
    wherein the holding portion comprises a recess on one end having a U-shaped cross-section and two open legs for receiving the rod, and a first inner thread on the open legs;
    wherein the locking element comprises a front end that faces out of the recess when fastened to the holding portion and an opposite back end that faces into the recess when fastened to the holding portion, a wall surrounding a central bore, an outer thread in a least one section of the wall, the outer thread cooperating with the first inner thread on the open legs, and a plurality of slits extending into the front end of the locking element substantially in an axial direction, one of the slits extending completely through the wall from the front end to the back end.

15. The holding device according to claim 14, wherein the locking element has a second inner thread, the holding device further comprising an inner screw having an exterior thread for cooperating with the inner thread of the locking element.

16. The holding device according to claim 15, wherein the shank portion and the holding portion are monoaxially connected.

17. The holding device according to claim 15, wherein the rod can be fixed by the inner screw of the locking element.

18. A holding device comprising:
    a shank portion;
    a holding portion connected to the shank portion for holding a rod; and
    a locking element to lock the rod in the holding portion;
    wherein the holding portion comprises a recess on one end having a U-shaped cross-section and two open legs for receiving the rod, and a first inner thread on the open legs;
    wherein the locking element comprises a front end that faces out of the recess when fastened to the holding portion and an opposite back end that faces into the recess when fastened to the holding portion, a wall surrounding a central bore, an outer thread in at least one section of the wall, the outer thread cooperating with the first inner thread on the open legs, and a slit extending substantially in an axial direction completely through the wall from the back end through the entire length of the outer thread in the at least one section of the wall.

* * * * *

UNITED STATES PATENT AND TRADEMARK OFFICE
CERTIFICATE OF CORRECTION

PATENT NO. : 7,223,268 B2 Page 1 of 1
APPLICATION NO. : 10/306060
DATED : May 29, 2007
INVENTOR(S) : Lutz Biedermann It is certified that error appears in the above-identified patent and that said Letters Patent is hereby corrected as shown below:

On The Title Page

(73) Assignee  Delete "Mötech"
  Insert --Motech--

Signed and Sealed this

Twenty Second Day of April, 2008

JON W. DUDAS
*Director of the United States Patent and Trademark Office*